United States Patent
Lambert et al.

(10) Patent No.: US 6,753,334 B2
(45) Date of Patent: Jun. 22, 2004

(54) PREPARATION OF SODIUM-HYDROGEN EXCHANGER TYPE-1 INHIBITORS

(75) Inventors: John F. Lambert, North Stonington, CT (US); Timothy Norris, Gales Ferry, CT (US)

(73) Assignees: Pfizer, Inc., New York, NY (US); Pfizer Products, Inc., Groton, CT (US)

( * ) Notice: Subject to any disclaimer, the term of this patent is extended or adjusted under 35 U.S.C. 154(b) by 0 days.

(21) Appl. No.: 09/995,133

(22) Filed: Nov. 27, 2001

(65) Prior Publication Data

US 2002/0082274 A1 Jun. 27, 2002

Related U.S. Application Data

(60) Provisional application No. 60/253,353, filed on Nov. 28, 2000.

(51) Int. Cl.[7] ................... C07D 215/38; C07D 215/12; A61K 31/47
(52) U.S. Cl. .................. 514/314; 546/167; 546/171
(58) Field of Search .................... 546/167, 171; 514/314

(56) References Cited

FOREIGN PATENT DOCUMENTS

| WO | 99/43663 | * | 9/1999 | |
| WO | WO 9943663 | | 9/1999 | ......... C07D/249/06 |

OTHER PUBLICATIONS

Weidenhagen, R., et al, [Journal name not indicated] 72(11):2010–2020, 1939, "339. On the Action of Diazonium Salts on Ascorbic Acid; A General Reaction of Dienols".

WO 99/43663A (*relevant part*—pg 58, pg 63 lines 26–30, examples 10, 13Q, 13P, 13W, 16A, 16Y, 19P, 30A, 32BB).

Baumgarth, M., et al., *J. Med. Chem.*, 40: 2017–2034, 1997.

Bream, J., et al., *Arzneim.–forsch.*, (Drug Res.) 25, Nr. 10, 1975.

Ferlin, M., et al., *Il Farmaco*, 44 (12): 1141–1155, 1989.

Menozzi, G., et al., *J. Heterocyclic Chem.*, 24, 1669–1675, 1987.

* cited by examiner

*Primary Examiner*—D. Margaret Seaman
(74) *Attorney, Agent, or Firm*—Scully, Scott, Murphy & Presser

(57) ABSTRACT

This invention relates to methods of preparing sodium-hydrogen exchanger type 1 (NHE-1) inhibitors of formula I'

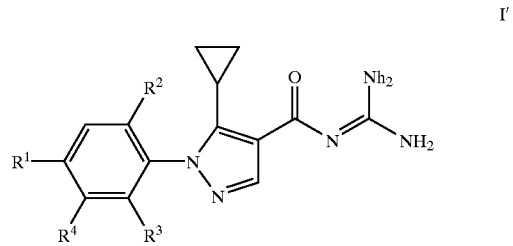

intermediates of the NHE-1 inhibitors and a new almost colorless form of the NHE-1 inhibitor N-(5-cyclopropyl-1-quinolin-5-yl-1H-pyrazole-4-carbonyl)-guanidine.

12 Claims, No Drawings

PREPARATION OF SODIUM-HYDROGEN EXCHANGER TYPE-1 INHIBITORS

This application is filed claiming priority from co-pending Provisional Application No. 60/253,353 filed Nov. 28, 2000.

FIELD OF THE INVENTION

This invention relates to methods of preparing sodium-hydrogen exchanger type 1 (NHE-1) inhibitors, intermediates of NHE-1 inhibitors and a new almost colorless form of the NHE-1 inhibitor, N-(5-cyclopropyl-1-quinolin-5-yl-1H-pyrazole-4-carbonyl)-guanidine.

BACKGROUND OF THE INVENTION

Sodium-hydrogen exchanger type 1 (NHE-1) inhibitors of formula I'

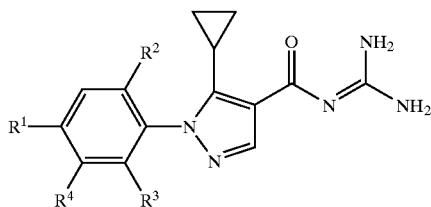

are useful for the prevention and treatment of myocardial ischemic injury. Myocardial ischemic injury can occur in out-patient as well as in perioperative settings and can lead to the development of sudden death, myocardial infarction or congestive heart failure. It is anticipated that therapies using the NHE-1 inhibitors of formula I' will be life-saving and reduce hospitalizations, enhance quality of life and reduce overall health care costs of high risk patients.

Commonly assigned WO 99/43663A1, the disclosure of which is hereby incorporated by reference, discloses a variety of NHE-1 inhibitors including the NHE-1 inhibitors of the present invention.

J. Med. Chem. 1997, 40, 2017–2034 "(2-Methyl-5-(methylsulfonyl)benzoyl)guanidine Na+/H+ Antiporter Inhibitors" and Arzneim.-Forsch. (Drug Res.) 25, Nr. 10 (1975) "Substituted Phenylacetylguanidines: a New Class of Antihypertensive Agents" disclose synthesizing acyl guanidine via coupling of an ester and guanidine, in addition to an acid chloride and guanidine wherein the substrates are aromatic monocyclic structures.

J. Heterocyclic Chem., 24, 1669 (1987) "Reaction of 2-Dimethylaminomethylene-1,3-diones with Dinucleophiles. VI. Synthesis of Ethyl or Methyl 1,5-Disubsittuted 1H-Pyrazole-4-carboxylates" discloses the preparation of esters of 5-substituted 1-phenyl-1H-pyrazole-4-carboxylic acids.

Ferlin, et al., II Famraco, 44:12, pp 1141–1156 (1989) discloses a method of synthesizing 5-hydrazinoquinoline by reacting quinolin-5-ylamine with stannous chloride and sodium nitrite.

When N-(5-cyclopropyl-1-quinolin-5-yl-1H-pyrazole-4-carbonyl)-guanidine, an NHE-1 inhibitor of formula I', is prepared by the previously known processes, colored impurities are produced. Aqueous solutions of N-(5-cyclopropyl-1-quinolin-5-yl-1H-pyrazole-4-carbonyl)-guanidine made by the previously known processes have a distinct yellow color. The impurities responsible for such coloration have not been identified.

From a commercial and regulatory point of view, discoloration of pharmaceutical products containing N-(5-cyclopropyl-1-quinolin-5-yl-1H-pyrazole-4-carbonyl)-guanidine is undesirable. In the case of pharmaceutical products that are administered to patients, especially products that are injected in patients' bodies, it is advantageous to have products that are almost colorless and whose active ingredient is in as pure a form as possible.

SUMMARY OF THE INVENTION

This invention relates to a novel process using ascorbic acid to prepare NHE-1 inhibitors of formula I'

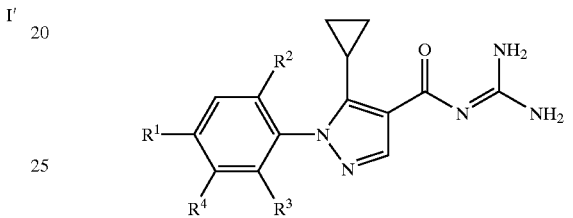

wherein $R^1$ is methylsulfonyl or hydrogen, $R^2$ is hydrogen or a halogen, $R^3$ is hydrogen, $R^4$ is hydrogen or a halogen, or $R^3$ and $R^4$ form, together with the carbon atoms to which they are attached, a six member fully unsaturated ring having one hetero atom that is nitrogen.

It has been discovered that when the NHE-1 inhibitor, N-(5-cyclopropyl-1-quinolin-5-yl-1H-pyrazole-4-carbonyl)-guanidine, is prepared by the ascorbic acid process of this invention, the final product has fewer colored impurities and is obtained in higher yield than that made by previous processes. It has also been discovered that by using citric acid in the preparation of N-(5-cyclopropyl-1-quinolin-5-yl-1H-pyrazole-4-carbonyl)-guanidine, these colored impurities are further reduced.

One aspect of this invention is methods of preparing compounds of formula VI'

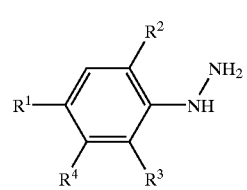

wherein $R^1$ is methylsulfonyl or hydrogen, $R^2$ is hydrogen or a halogen, $R^3$ is hydrogen, $R^4$ is hydrogen or a halogen, or $R^3$ and $R^4$ form, together with the carbon atoms to which they are attached, a six member fully unsaturated ring having one hetero atom that is nitrogen, comprising reducing, with ascorbic acid, compounds of formula II'

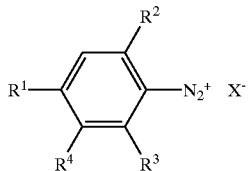

wherein X is chloride, bromide, iodide, ½(SO$_4$)$^{2-}$ or tetrafluoroborate and R$^1$, R$^2$, R$^3$ and R$^4$ are as defined for formula VI' above.

Another aspect of the invention is methods of preparing compounds of formula VI', comprising combining compounds formula II', with ascorbic acid to form compounds of formula V'

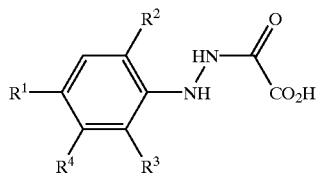

wherein R$^1$, R$^2$, R$^3$ and R$^4$ are as defined for formula VI' above, and heating the compound of formula V' to a temperature above about 50° C. to form compounds of formula VI'.

A further aspect of the invention is methods of preparing compounds of formula I'

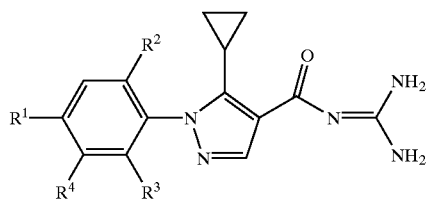

wherein R$^1$, R$^2$, R$^3$ and R$^4$ are as defined for formula VI' above, comprising combining the compound of formula VI' made by a method of this invention, with α-[(dimethylamino)methylene]-β-oxo-cyclopropanepropanoic acid, (αZ)-methylester to form compounds of formula VIII'

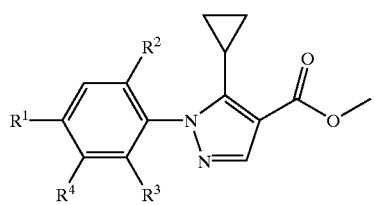

wherein R$^1$, R$^2$, R$^3$ and R$^4$ are as defined for formula VI' above, and coupling said formula VIII' compound with guanidine to form the compound of formula I'.

A still further aspect of this invention is compounds of formula V'

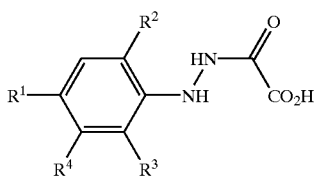

wherein R$^1$, R$^2$, R$^3$ and R$^4$ are as defined for formula VI' above.

Another aspect of this invention is compounds of formula IV'

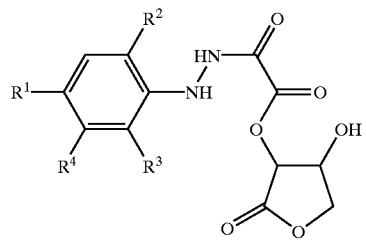

wherein R$^1$, R$^2$, R$^3$ and R$^4$ are as defined for formula VI' above.

A further aspect of this invention is methods of preparing 5-hydrazinoquinoline comprising reduction of a diazonium salt of 5-aminoquinoline with ascorbic acid.

An additional aspect of this invention is methods of preparing 5-hydrazinoquinoline comprising combining a diazonium salt of 5-aminoquinoline with ascorbic acid to form [2-(5-quinolinyl)hydrazide]-ethanedioic acid and heating said [2-(5-quinolinyl)hydrazide]-ethanedioic acid to a temperature above about 35° C., preferably above about 50° C. and most preferably above about 80° C., in an aqueous solution containing a hydrolyzing agent, preferably hydrochloric acid.

Another aspect of this invention is methods of preparing [2-(5-quinolinyl)hydrazide]-ethanedioic acid comprising combining a diazonium salt of 5-aminoquinoline with ascorbic acid to form a reaction mixture and maintaining said reaction mixture at a temperature below about 25° C.

A further aspect of this invention is the compound [2-(5-quinolinyl)hydrazide]-ethanedioic acid.

A still further aspect of this invention is the compound of formula IV

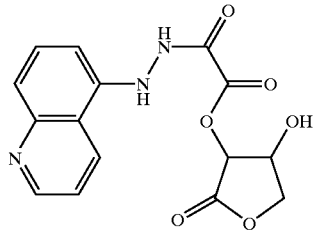

An additional aspect of this invention is methods of preparing N-(5-cyclopropyl-1-quinolin-5-yl-1H-pyrazole-4-carbonyl)-guanidine comprising:
  combining 5-hydrazinoquinoline made by a method of this invention with α-[(dimethylamino)methylene]-β- oxo-cyclopropanepropanoic acid, (αZ)-methyl ester to form 5-cyclopropyl-1-quinolin-5-yl-1H-pyrazole-4-carboxylic acid methyl ester; and coupling said 5-cyclopropyl-1-quinolin-5-yl-1H-pyrazole-4-carboxylic acid methyl ester with guanidine to form N-(5-cyclopropyl-1-quinolin-5-yl-1H-pyrazole-4-carbonyl)-guanidine.

Another aspect of this invention is methods of preparing N-(5-cyclopropyl-1-quinolin-5-yl-1H-pyrazole-4-carbonyl)-guanidine comprising:

combining 5-hydrazinoquinoline made by a method of this invention with α-[(dimethylamino)methylene]-β-oxo-cyclopropanepropanoic acid, (αZ)-methyl ester to form 5-cyclopropyl-1-quinolin-5-yl-1H-pyrazole-4-carboxylic acid methyl ester;

hydrolyzing said 5-cyclopropyl-1-quinolin-5-yl-1H-pyrazole-4-carboxylic acid methyl ester with an inorganic base to form 5-cyclopropyl-1-quinolin-5-yl-1H-pyrazole-4-carboxylic acid; and coupling said 5-cyclopropyl-1-quinolin-5-yl-1H-pyrazole-4-carboxylic acid with guanidine to form N-(5-cyclopropyl-1-quinolin-5-yl-1H-pyrazole-4-carbonyl)-guanidine.

A further aspect of this invention is methods of preparing N-(5-cyclopropyl-1-quinolin-5-yl-1H-pyrazole-4-carbonyl)-guanidine comprising:

treating 5-cyclopropyl-1-quinolin-5-yl-1H-pyrazole-4-carboxylic acid methyl ester with citric acid to form purified 5-cyclopropyl-1-quinolin-5-yl-1H-pyrazole-4-carboxylic acid methyl ester; and coupling said purified 5-cyclopropyl-1-quinolin-5-yl-1H-pyrazole-4-carboxylic acid methyl ester with guanidine to form N-(5-cyclopropyl-1-quinolin-5-yl-1H-pyrazole-4-carbonyl)-guanidine.

Another aspect of this invention is methods of preparing N-(5-cyclopropyl-1-quinolin-5-yl-1H-pyrazole-4-carbonyl)-guanidine comprising:

treating 5-cyclopropyl-1-quinolin-5-yl-1H-pyrazole-4-carboxylic acid methyl ester with citric acid to form purified 5-cyclopropyl-1-quinolin-5-yl-1H-pyrazole-4-carboxylic acid methyl ester;

hydrolyzing said purified 5-cyclopropyl-1-quinolin-5-yl-1H-pyrazole-4-carboxylic acid methyl ester with an inorganic base to form 5-cyclopropyl-1-quinolin-5-yl-1H-pyrazole-4-carboxylic acid; and coupling said 5-cyclopropyl-1-quinolin-5-yl-1H-pyrazole-4-carboxylic acid with guanidine to form N-(5-cyclopropyl-1-quinolin-5-yl-1H-pyrazole-4-carbonyl)-guanidine.

A still further aspect of this invention is methods of preparing N-(5-cyclopropyl-1-quinolin-5-yl-1H-pyrazole-4-carbonyl)-guanidine comprising:

treating 5-cyclopropyl-1-quinolin-5-yl-1H-pyrazole-4-carboxylic acid methyl ester dissolved in an inert solvent, preferably ethyl acetate, with citric acid dissolved in an aqueous solution to form purified 5-cyclopropyl-1-quinolin-5-yl-1H-pyrazole-4-carboxylic acid methyl ester, wherein said 5-cyclopropyl-1-quinolin-5-yl-1H-pyrazole-4-carboxylic acid methyl ester is preferably prepared by combining 5-hydrazinoquinoline made by a method of this invention with α-[(dimethylamino)methylene]-β-oxo-cyclopropanepropanoic acid, (αZ)-methyl ester;

hydrolzying said purified 5-cyclopropyl-1-quinolin-5-yl-1H-pyrazole-4-carboxylic acid methyl ester with an inorganic base, preferably selected from sodium hydroxide, lithium hydroxide and potassium hydroxide and preferably wherein the base is dissolved in a solvent selected from water, methanol and tetrahydrofuran, to form 5-cyclopropyl-1-quinolin-5-yl-1H-pyrazole-4-carboxylic acid;

treating said 5-cyclopropyl-1-quinolin-5-yl-1H-pyrazole-4-carboxylic acid with a coupling agent to form an activated compound that is reactive with guanidine;

coupling the activated compound with guanidine to form N-(5-cyclopropyl-1-quinolin-5-yl-1H-pyrazole-4-carbonyl)-guanidine.

An additional aspect of this invention is methods of preparing 2-chloro-4-methanesulfonyl-2-phenylhydrazine comprising reduction of a diazonium salt of 2-chloro-4-methanesulfonyl-phenylamine with ascorbic acid.

Another aspect of this invention is methods of preparing 2-chloro-4-methanesulfonyl-2-phenylhydrazine comprising:

combining a diazonium salt of 2-chloro-4-methanesulfonyl-phenylamine with ascorbic acid to form mono [2-[2-chloro-4-(methyl sulfonyl)phenyl]hydrazide]ethanedioic acid; and heating said [2-[2-chloro-4-(methyl sulfonyl)phenyl]hydrazide]ethanedioic acid to a temperature above about 35° C., preferably above about 50° C. and most preferably above about 80° C., in an aqueous solution containing a hydrolyzing agent, preferably hydrochloric acid, to form 2-chloro-4-methanesulfonyl-2-phenylhydrazine.

A further aspect of this invention is methods of preparing [2-[2-chloro-4-(methyl sulfonyl)phenyl]hydrazide] ethanedioic acid comprising combining a diazonium salt of 2-chloro-4-methanesulfonyl-phenylamine with ascorbic acid to form a reaction mixture and maintaining said reaction mixture at a temperature below about 25° C.

A still further aspect of this invention is methods of preparing N-{5-cyclopropyl-1-(2-chloro-4-methanesulfonylphenyl)-1H-pyrazole-4-carbonyl}-guanidine comprising:

combining 2-chloro-4-methanesulfonyl-2-phenylhydrazine made by a method of this invention with α-[(dimethylamino)methylene]-β-oxo-cyclopropanepropanoic acid, (αZ)-methyl ester to form 5-cyclopropyl-1-(2-chloro-4-methanesulfonylphenyl)-1H-pyrazole-4-carboxylic acid methyl ester; and coupling said 5-cyclopropyl-1-(2-chloro-4-methanesulfonylphenyl)-1H-pyrazole-4-carboxylic acid methyl ester with guanidine to form N-{5-cyclopropyl-1-(2-chloro-4-methanesulfonylphenyl)-1H-pyrazole-4-carbonyl}-guanidine.

An additional aspect of this invention is methods of preparing N-{5-cyclopropyl-1-(2-chloro-4-methanesulfonylphenyl)-1H-pyrazole-4-carbonyl}-guanidine comprising:

combining 2-chloro-4-methanesulfonyl-2-phenylhydrazine made by a method of this invention with α-[(dimethylamino)methylene]-β-oxo-cyclopropanepropanoic acid, (αZ)-methyl ester to form 5-cyclopropyl-1-(2-chloro-4-methanesulfonylphenyl)-1H-pyrazole-4-carboxylic acid methyl ester;

hydrolyzing said 5-cyclopropyl-1-(2-chloro-4-methanesulfonylphenyl)-1H-pyrazole-4-carboxylic acid methyl ester with an inorganic base to form 5-cyclopropyl-1-(2-chloro-4-methanesulfonylphenyl)-1H-pyrazole-4-carboxylic acid; and coupling said 5-cyclopropyl-1-(2-chloro-4-methanesulfonylphenyl)-1H-pyrazole-4-carboxylic acid with guanidine to form N-(5-cyclopropyl-1-quinolin-5-yl-1H-pyrazole-4-carbonyl)-guanidine.

Another aspect of this invention is N-(5-cyclopropyl-1-quinolin-5-yl-1H-pyrazole-4-carbonyl)-guanidine and pharmaceutically acceptable salts thereof, preferably N-(5-cyclopropyl-1-quinolin-5-yl-1H-pyrazole-4-carbonyl)-guanidine monomesylate, having a light absorption at 450 nanometers in a 1% water solution at 25° C. of less than about 0.02 and preferably less than about 0.01.

Another aspect of this invention is a pharmaceutical composition comprising N-(5-cyclopropyl-1-quinolin-5-yl-1H-pyrazole-4-carbonyl)-guanidine and pharmaceutically acceptable salts thereof, preferably N-(5-cyclopropyl-1-quinolin-5-yl-1H-pyrazole-4-carbonyl)-guanidine monomesylate, having a light absorption at 450 nanometers in a 1% water solution at 25° C. of less than about 0.02 and preferably less than about 0.01 and a pharmaceutically acceptable vehicle, diluent or carrier.

A still further aspect of this invention is a method of reducing tissue damage resulting from ischemia or hypoxia comprising administering to a mammal in need of such treatment a therapeutically effective amount of N-(5-cyclopropyl-1-quinolin-5-yl-1H-pyrazole-4-carbonyl)-guanidine and pharmaceutically acceptable salts thereof, preferably N-(5-cyclopropyl-1-quinolin-5-yl-1H-pyrazole-4-carbonyl)-guanidine monomesylate, having less than a light absorption at 450 nanometers of less than about 0.02 and preferably less than about 0.01 in a 1% water solution at 25° C., or a pharmaceutically acceptable composition comprising said compound.

In a preferred embodiment of the method aspects of this invention said ascorbic acid is L-ascorbic acid.

The term "inert solvent" refers to a solvent system in which the components do not interact with starting materials, reagents, intermediates or products in a manner which adversely affects the yield of the desired product.

The term "light absorption" refers to the absorption of light in a solution as calculated by the formula, $A=\log_{10}(I_0/I)$, wherein "$I_0$" is incident light and "I" is transmitted light. This formula is derived from the equation, $\log_{10}(I_0/I)=\epsilon \cdot l \cdot c$, wherein $\epsilon$ is the molar extinction coefficient of the solution in $cm^2$/mole, I is the path length of the absorbing solution in centimeters and c is the concentration in moles/liter.

The expression "pharmaceutically-acceptable salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluenesulfonate. Where more than one basic moiety exists, the expression includes multiple salts (e.g., di-salt). The expression also refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methylglucamine), benethamine (N-benzylphenethylamine), piperazine or tromethamine (2-amino-2-hydroxymethyl-1,3-propanediol).

The term "purified" when used in connection with 5-cyclopropyl-1-quinolin-5-yl-1H-pyrazole-4-carboxylic acid methyl ester means 5-cyclopropyl-1-quinolin-5-yl-1H-pyrazole-4-carboxylic acid methyl ester that has been treated so as to reduce the presence of colored impurities.

Those skilled in the art will recognize that certain compounds of this invention will contain one or more atoms that may be in a particular stereochemical or geometric configuration, giving rise to stereoisomers and configurational isomers. All such isomers and mixtures thereof are included in this invention.

DETAILED DESCRIPTION OF THE INVENTION

Reaction Scheme A illustrates the process of preparing compounds of formula VI'. Scheme B illustrates the process of preparing compounds of formula I' using compounds of formula VI' from Scheme A. This process is used to make NHE-1 inhibitors, including N-(5-cyclopropyl-1-quinolin-5-yl-1H-pyrazole-4-carbonyl)-guanidine.

SCHEME A

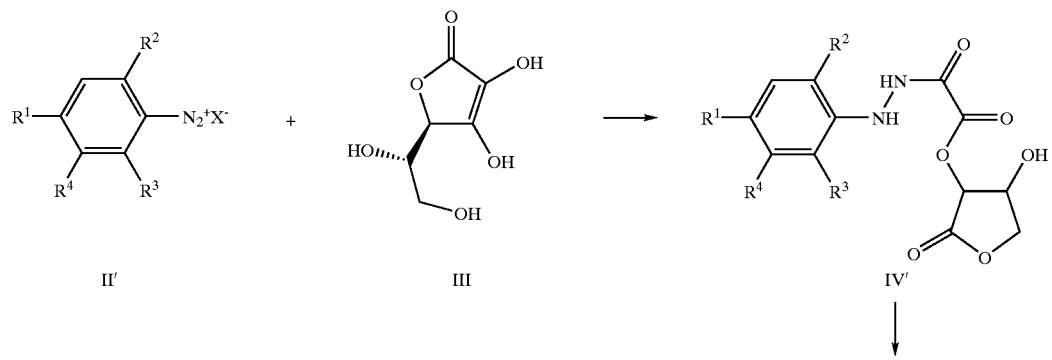

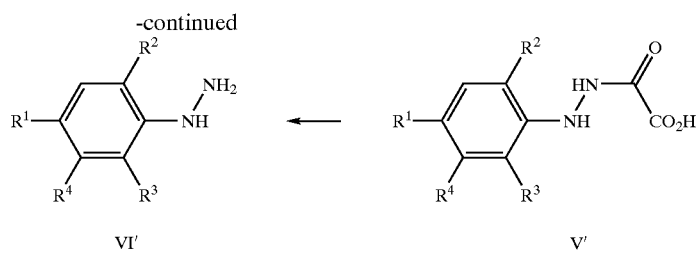

SCHEME B

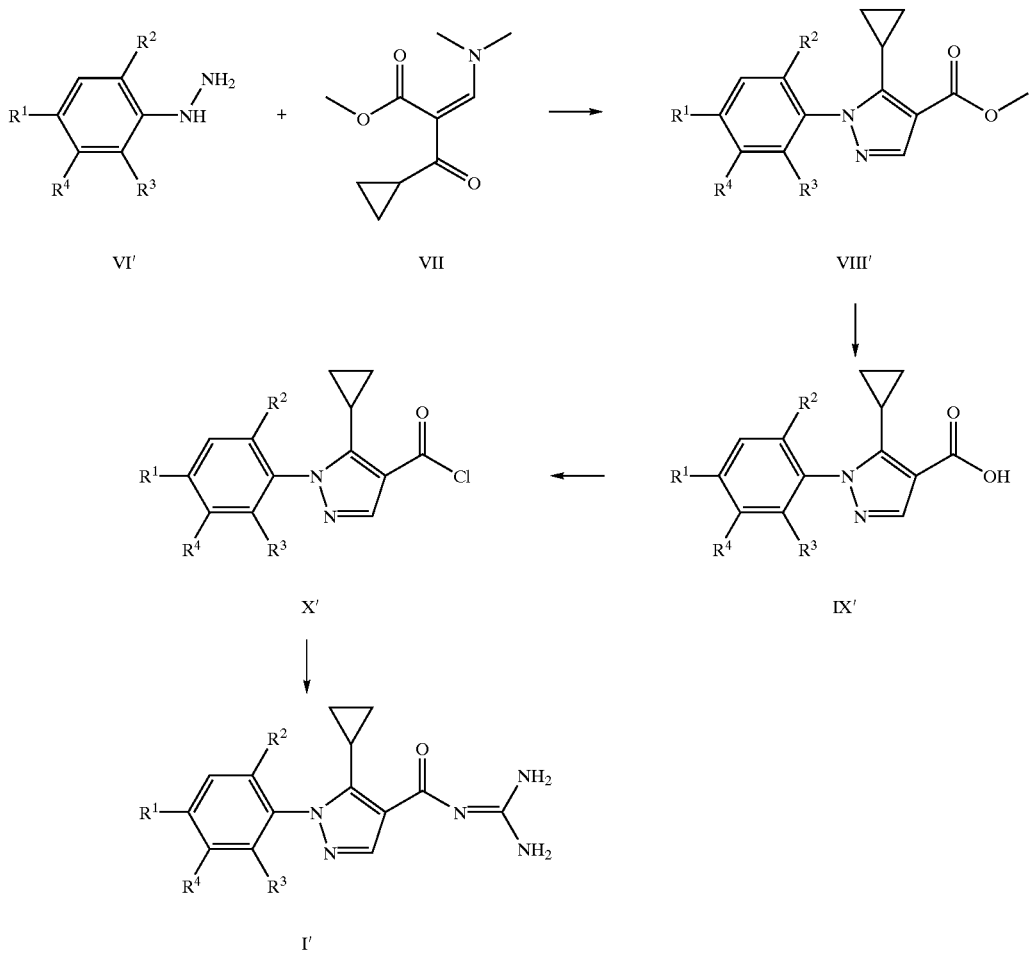

According to Scheme A, a diazonium salt of formula II' is combined with L-ascorbic acid (formula III) to form the lactone intermediate compounds of formula IV' as a transient intermediate, which decomposes to the formula V' oxalic acid intermediate. At elevated reaction temperatures, above about 35° C. and preferably above about 50° C. and most preferably above about 80° C., the formula IV' compounds convert to the formula VI' compound as a one-pot reaction. At lower temperatures, the formula V' oxalic acid intermediate compounds are not converted to the formula VI' compound. The formula V' oxalic compound may be converted to the formula VI' hydrazino compound as the hydrochloride by hydrolysis with concentrated hydrochloric acid.

The lactone intermediates of formula IV' are unstable and decompose under the reaction conditions into the oxalic acid derivative. However, when the diazonium salt of formula II' derived from 2,5-dichlorophenylaniline is used to make the formula II' diazonium salt, it is possible to isolate the lactone intermediate. NMR analysis of this compound gives results that are consistent with a lactone structure.

Scheme B illustrates the process of preparing the compound of formula I'. The formula VI' hydrazino compound is combined with the formula VII compound in an inert solvent such as ethyl acetate at a temperature of about 20° C. for about one hour followed by heating to a temperature of about 75° C. for about five hours to form the formula VIII' pyrazole compound.

The formula VII compound may be prepared by combining methyl-3-cyclopropyl-3-oxopropanoate in ethyl acetate with N,N-dimethylformamide dimethylacetal at about 65° C. to about 75° C. for about 4 hours.

The formula VIII' pyrazole is hydrolyzed with a base such as sodium hydroxide, lithium hydroxide or potassium hydroxide in a solvent such as water and/or methanol and/or THF conveniently at ambient temperature or at elevated temperature (e.g., reflux) for about one hour to about five hours to prepare the formula IX' acid.

The formula IX' acid is activated with a coupling agent such as thionyl chloride at a temperature of about 60° C. to about 90° C. for about 13 hours to form the formula X' acid chloride. Other suitable coupling agents may be used. A suitable coupling agent is one which transforms the carboxylic acid into a reactive species which forms an acyl guanidine on reaction with guanidine. The coupling agent can convert the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric flouride to form an acid flouride or an alkyl chloroformate such as isobutyl or isopropenyl chloroformate or propanephosphonic anhydride to form a mixed anhydride of the carboxylic acid, or carbonyldimidazole to form an acylimidazole. Alternatively, the coupling agent may be a reagent which effects coupling in a one pot process. Exemplary coupling reagents are 1-(3-dimethylaminopropyl)-3-ethylcarbodiimide hydrochloride-hydroxybenzotriazole (EDC/HOBT), dicyclohexylcarbodiimide/hydroxybenzotriazole (DCC/HOBT),2-ethoxy-1-ethoxycarbonyl-,2dihydroquinoline (EEDQ) and diethylphosphorylcyanide. The coupling is performed in an inert solvent, preferably an aprotic solvent, in the presence of excess guanidine. Exemplary solvents include acetonitrile, dichloromethane, dimethylformamide and chloroform or mixtures thereof. Use of these coupling agents and appropriate selection of solvents and temperatures are known to those skilled in the art or can be readily determined from the literature in light of this disclosure. These and other exemplary conditions useful for coupling carboxylic acids are described in Houben-Weyl, Vol XV, part II, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

The formula X compound is coupled with guanidine to form the NHE-1 inhibitor of formula I' by combining the formula X' compound with guanidine hydrochloride and an inorganic base such as sodium hydroxide, lithium hydroxide or potassium hydroxide in a solvent which is preferably selected from water, methanol and tetrahydrofuran.

In a preferred embodiment of the reactions of Scheme A and Scheme B, the formula II' compound is a diazonium salt of 5-aminoquinoline. The diazonium salt of 5-aminoquinoline is combined with ascorbic acid to form the compound of formula VI' that is 5-hydrazinoquinoline. The formula VIII' pyrazole formed is 5-cyclopropyl-1-quinolin-5-yl-1H-pyrazole-4-carboxylic acid methyl ester. Prior to the coupling step with guanidine, 5-cyclopropyl-1-quinolin-5-yl-1H-pyrazole-4-carboxylic acid methyl ester is preferably treated with citric acid to remove red impurities. In this treatment, the solvent solution containing 5-cyclopropyl-1-quinolin-5-yl-1H-pyrazole-4-carboxylic acid methyl ester is combined with an aqueous solution of citric acid to form a darker red aqueous layer and a red organic layer. The aqueous layer is discarded.

The citric acid purified 5-cyclopropyl-1-quinolin-5-yl-1H-pyrazole-4-carboxylic acid methyl ester is hydrolyzed with a base such as sodium hydroxide in water to form 5-cyclopropyl-1-quinolin-5-yl-1H-pyrazole-4-carboxylic acid, analogous to the formula IX' acid. 5-Cyclopropyl-1-quinolin-5-yl-1H-pyrazole-4-carboxylic acid is then activated with a coupling agent such as thionyl chloride to form the chloride compound, analogous to the formula X' compound. The chloride activated compound is then coupled with guanidine to form the NHE-1 inhibitor, N-(5-cyclopropyl-1-quinolin-5-yl-1H-pyrazole-4-carbonyl)-guanidine.

N-(5-Cyclopropyl-1-quinolin-5-yl-1H-pyrazole-4-carbonyl)-guanidine prepared by a method of this invention may be converted to pharmaceutically acceptable salts. For example N-(5-cyclopropyl-1-quinolin-5-yl-1H-pyrazole-4-carbonyl)-guanidine may be converted to its mesylate salt by combining the compound with methanesulfonic acid, preferably in a polar aprotic solvent at a temperature of about 40° C. to about 80° C. The polar aprotic solvent is preferably a mixture of acetone and 1-methyl-2-pyrrolidonone. Conversion to other pharmaceutically acceptable salts may be performed by processes known in the art.

N-(5-Cyclopropyl-1-quinolin-5-yl-1H-pyrazole-4-carbonyl)-guanidine monomesylate, when prepared by the chemical processes and methods outlined above, gives rise to 1% aqueous solutions with very low blue light absorption. At 450 nm the light absorption of a 1% solution is in the range 0.007–0.005. Previous procedures gave rise to distinctly yellow solutions with absorption levels in the range 0.027–0.025. Light absorption is calculated according to the formula, $A=\log_{10}(I_0/I)$, wherein "$I_0$" is incident light and "I" is transmitted light.

In another preferred embodiment, the formula II' compound is a diazonium salt of 2-chloro-4-methanesulfonyl-phenylamine. The diazonium salt is combined with ascorbic acid to form the compound of formula VI' that is 2-chloro-4-methanesulfonyl-2-phenylhydrazine. The formula VIII' pyrazole formed is 5-cyclopropyl-1-(2-chloro-4-methanesulfonylphenyl)-1H-pyrazole-4-carboxylic acid methyl ester.

5-Cyclopropyl-1-(2-chloro-4-methanesulfonylphenyl)-1H-pyrazole-4-carboxylic acid methyl ester is hydrolyzed with a base such as sodium hydroxide in water to form 5-cyclopropyl-1-(2-chloro-4-methanesulfonylphenyl)-1H-pyrazole-4-carboxylic acid, analogous to the formula IX' acid. The carboxylic acid pyrazole is then activated with coupling agent such as thionyl chloride to form the activated compound, analogous to the formula X' compound. The activated compound is then coupled with guanidine to form the NHE-1 inhibitor, N-{5-cyclopropyl-1-(2-chloro-4-methanesulfonylphenyl)-1H-pyrazole-4-carbonyl}-guanidine.

An alternative, which is not shown in Scheme B, is the direct conversion of the Formula VII' pyrazole to the NHE-1 inhibitor of Formula I' by several methods. For example, the Formula VIII' pyrazole can be heated in the presence of excess guanidine, in a polar protic solvent for example, methanol or isopropanol, at a suitable temperature, conveniently at reflux for about one to about seventy-two hours. This transformation may also be performed by repeatedly removing the solvent, for example, removing ethanol or toluene, about four times from a mixture of the Formula VIII' pyrazole and excess guanidine at a pressure of about one to about 100 mmHg and at a temperature of about 25° C. to about 95° C. This reaction may also be performed in the absence of solvent by heating the mixture of the formula VIII' pyrazole and excess guanidine at a temperature of about 100° C. to about 180° C., optionally at a pressure of about 1 to about 100 mmHg for about five minutes to about eight hours.

The starting material and reagents for the above described compounds are readily available or can be easily synthesized by those skilled in the art using conventional methods of organic synthesis.

Administration of the compounds prepared by a method of this invention can be via any method which delivers a compound of this invention preferentially to the desired tissue (e.g., liver and/or cardiac tissues). These methods include oral routes, parenteral, intraduodenal routes, etc. Generally, the compounds of the present invention are administered in single (e.g., once daily) or multiple doses or via constant infusion.

The compounds prepared by a method of this invention are useful, for example, in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The active compound is therefore usefully employed prophylactically to prevent, i.e. (prospectively or prophylactically) to blunt or stem, tissue damage (e.g., myocardial tissue) in patients who are at risk for ischemia (e.g., myocardial ischemia).

Generally, the compounds prepared by a method of this invention are administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

The amount and timing of compounds administered will, of course, be dependent on the subject being treated, on the severity of the affliction, on the manner of administration and on the judgement of the prescribing physician. Thus, because of patient to patient variability, the dosages given below are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases (e.g., cardiovascular disease).

For example, in one mode of administration, the compounds prepared by a method of this invention may be administered just prior to surgery (e.g., within twenty-four hours before surgery for example cardiac surgery) during or subsequent to surgery (e.g., within twenty-four hours after surgery) where there is risk of myocardial ischemia. The compounds may also be administered in a chronic daily mode.

Amounts of the compounds prepared by a method of this invention are used that are effective for ischemic protection. A preferred dosage is about 0.001 to 100 mg/kg/day of the compounds. An especially preferred dosage is about 0.01 to 50 mg/kg/day of the compounds.

The compounds of the present invention are generally administered in the form of a pharmaceutical composition comprising at least one of the compounds of this invention together with a pharmaceutically acceptable vehicle, carrier or diluent. Thus, the compounds of this invention can be administered individually or together in any conventional oral, parenteral, rectal or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions, for example, in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

For purposes of transdermal (e.g.,topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington: The Science and Practice of Pharmacy,* Mack Publishing Company, Easton, Pa., 19th Edition 1995.

Pharmaceutical compositions according to the invention may contain for example 0.0001%–95% of the compounds prepared by a method of this invention. In any event, the composition or formulation to be administered will contain a quantity of the compound(s) prepared according to the invention in an amount effective to treat the disease/condition of the subject being treated.

EXPERIMENTAL PROCEDURES

NMR spectra were recorded on a Varian XL-300 (Varian Co., Palo Alto, Calif.), a Bruker AM-300 spectrometer (Bruker Co., Billerica, Mass.) or a Varian Unity 400 at about 23° C. at 300 or 400 MHz for proton. Chemical shifts are expressed in parts per million downfield from trimethylsilane. The peak shapes are denoted as follows: s=singlet; d=doublet; t=triplet, q=quartet; m=multiplet; bs=broad singlet.

EXAMPLE 1

Preparation of a Mixture Containing [2-(5-quinolinyl) hydrazide]-ethanedioic acid, monohydrochloride and 5-hydrazinoquinoline dihydrochloride In a 1 liter round-bottomed flask equipped with mechanical stirrer, thermometer, reflux condenser and under a nitrogen atmosphere, concentrated hydrochloric acid (32%) (300 ml) was charged. The reaction was performed under continuous nitrogen flow. After cooling to 0±2° C., 5-aminoquinoline (50 g) was charged in one portion. An exotherm was observed, with an increase in temperature from 0±2° C. up to 25–26° C. A pink suspension was obtained. The reaction mixture was re-cooled to 0±2° C. and a solution of sodium nitrite (29 g) in water (50 ml) was added to the acidic solution over a period of 30 minutes, while maintaining the temperature at 0±2° C. During sodium nitrite addition, brown fumes and a slight effervescence were observed. The suspension color turned from strawberry-red to deep brown-red. The reaction was stirred for 1 h at 0±2° C. Then, L-ascorbic acid (50 g) was added portionwise over a period of 30 minutes. The addition of the first portion of L-ascorbic (1–2 grams) led to effervescence, while the next portions (about 5 grams each) could be added faster as effervescene was not significant. A small exotherm was observed. The reaction mixture (brown-red suspension) was stirred at 0±2° C. for 5–10 minutes, then it was allowed to come to room temperature (18–22° C.) spontaneously in about 40 minutes. Finally, it was heated to 38–42° C. and stirred 3 hours at this temperature. Product precipitation was observed after about 30 minutes at 38–42° C., leading to formation of an orange suspension. After 3 hours at 38–40° C. the reaction was deemed complete by HPLC analysis calculated by area percent: 90% (sum of oxalic acid intermediate and 5-hydrazinoquinoline); lactone intermediate:<3%). The reaction mixture was cooled to room temperature (18–22° C.) and water (100 ml) was added. The slurry was stirred for 16 hours at 20±2° C., then cooled to 0–2° C. and stirred 1.5 hours at 0–2° C. Optionally, after the addition of water, the mixture is directly cooled to 0–2° C. and stirred 1–2 hours at this temperature. The product was filtered and washed with methanol (2×30 ml), thus obtaining 107 g of wet product.

Ten grams of the wet product was dried in an air tray drier overnight (16 hours) at 40° C. leading to 7.8 g of a mixture of the oxalic acid intermediate, [2-(5-quinolinyl)hydrazide]-ethanedioic acid, mono hydrochloride and 5-hydrazinoquinoline dihydrochloride, as orange crystals.

The other 97 g of wet product was hydrolized directly to 5-hydrazinoquinoline dihydrochloride according to Example 2.

HPLC (calculated as area percent):

76.7% oxalic acid intermediate, [2-(5-quinolinyl) hydrazide]-ethanedioic acid, mono hydrochloride;

22.0% 5-hydrazinoquinoline dihydrochloride.

Molar Yield (calculated as HPLC area percent): 91.8%

EXAMPLE 2

Preparation of essentially pure 5-hydrazinoquinoline dihydrochloride from Mixture of [2-(5-quinolinyl)hydrazide]-ethanedioic acid mono hydrochloride and 5-hydrazinoquinoline dihydrochloride In a 1 L round-bottomed flask equipped with mechanical stirrer, thermometer, reflux condenser and under a nitrogen atmosphere, wet product from Example 1, (97.0 g, corresponding to 75.7 g of dry product), water (100 ml) and concentrated hydrochloric acid, 32% (300 ml) were charged. The yellow suspension was heated to 90±2° C. and stirred 1.5 hours at this temperature. During hydrolysis, the color of the suspension turned from orange-yellow to deep yellow and a density increase of the slurry was observed. The mixture was cooled to room temperature (20±2° C.) and stirred 2 hours at this temperature. The solid was filtered, washed with methanol (3×30 ml) and dried for 16 hours in an air tray drier at 40° C.

Yield:

61.3 g of 5-hydrazinoquinoline dihydrochloride, as yellow crystalline solid.

Molar Yield:

91.5% hydrolysis yield 83.9% overall yield (based on 5-aminoquinoline)

EXAMPLE 3

Preparation of Essentially Pure [2-(5-quinolinyl)hydrazide]-ethanedioic acid, mono hydrochloride To a 250 ml flask under a nitrogen atmosphere, water (20 ml) and concentrated HCl (60 ml, 32%, 0.61 moles) were charged and cooled down to −2 to 0° C. 5-Aminoquinoline (10 g, 0.069 moles) was added in one portion as a solid. An exotherm of 10° C. was observed. The acidic suspension was re-cooled to −2 to 0° C. and sodium nitrite (5.8 g, 0.084 moles) dissolved in water (10 ml) was added dropwise to the acidic mixture through an addition funnel over a period of 20 minutes at −2 to 0° C. The resulting mixture was stirred for 1 hour at −2 to 0° C. L-Ascorbic acid (14.3 g, 0.081 moles) was then added in portions as a solid at −2 to 0° C. The reaction was allowed to come to room temperature (18–20° C.) and then stirred for 48 hours to form an orange suspension. The product was filtered, washed with water (50 ml) and dried to constant weight in an air tray drier at 40° C. to afford 12.7 g of oxalic acid derivative (HPLC analysis calculated as area percent: 99.7%; 68.4% molar yield).

$^1$H-NMR (DMSO-$d_6$), 11.10 (s, 1H), 9.57 (br. S, NH), 9.45 (d, J=8.41 Hz, 1H), 9.21 (d, J=5.29 Hz, 1H), 7.96 (m, 2H), 7.40 (d, J=8.4 Hz, 1H), 6.98 (d, J=7.8, 1H)

EXAMPLE 4

Preparation of 5-hydrazinoquinoline dihydrochloride

To a 250 ml flask under a nitrogen atmosphere, water (20 ml) and concentrated HCl (60 ml, 0.61 moles) were charged and cooled down to −2 to 0° C. 5-Aminoquinoline (10 g, 0.069 moles) was added in one portion as a solid. An increase in temperature of 10° C. was observed. The orange-yellow suspension was re-cooled to −2 to 0° C. and sodium nitrite (5.8 g, 0.084 moles) dissolved in water (10 ml) was added dropwise to the acidic solution through an addition funnel over a period of 20 minutes at −2 to 0° C. The resulting mixture (dark-brown solution) was stirred for 1 hour at −2 to 0° C. L-Ascorbic acid (14.3 g, 0.081 moles) was then added in portions as a solid over a period of 20 minutes at −2 to 0° C. The reaction was allowed to come to room temperature (18–20° C.) over a period of 30 minutes, then heated at 50° C. and stirred for 30 hours at this temperature. The resultant slurry was cooled to room temperature (18–20° C.), stirred for 1 hour at this temperature, filtered and washed with propan-2-ol (40 ml). The product was dried to constant weight in an air tray drier at 40° C. to afford 11.75 g of 5-hydrazinoquinoline dihydrochloride as a green solid (HPLC purity calculated as area percent: 98%, with 1.6% of oxalic acid intermediate; 71.5% molar yield).

EXAMPLE 5

Preparation of 5-hydrazinoquinoline dihydrochloride

To a 1 L flask under a nitrogen atmosphere, concentrated HCl (300 ml, 32%, 3.05 moles) was charged and cooled to −2 to 0° C. 5-Aminoquinoline (50 g, 0.347 moles) was then added all at once as a solid. An increase in temperature of 25° C. was observed. The suspension was again cooled to −2 to 0° C. Aqueous sodium nitrite (29 g, 0.420 moles) dissolved in water (50 ml) was added dropwise to the acidic solution through an addition funnel over a period of 1 hour at −2 to 0° C. The resulting mixture (dark-brown solution)

was stirred for 1 hour at −2 to 0° C. L-Ascorbic acid (64 g, 0.363 moles) was then added in portions as a solid over a period of 1 hour at (−)2–0° C. The reaction was allowed to come to room temperature (18–20° C.) over a period of 45 minutes, then heated at 80° C. and stirred 20 minutes at this temperature. The resultant orange suspension was cooled to room temperature (18–20° C.) and water (100 ml) was added. The slurry was stirred overnight (16–17 hours) at 18–20° C., cooled to 0° C. for 1.5 hours, filtered and washed with methanol (150 ml). The product was dried to constant weight in an air tray drier at 40° C. to afford 53.8 g of 5-hydrazinoquinoline dihydrochloride as a green-brown solid (HPLC purity calculated as area percent: 98.6%, with 1.3% of oxalic acid intermediate; 66% molar yield).

EXAMPLE 6

Preparation of 2,5-dichlorophenylhydrazine lactone intermediate

Concentrated HCl (45 ml, 32%, 458 mmoles) and water (270 ml) were charged to a 500 ml flask under a nitrogen atmosphere and cooled to −2 to 0° C. 2,5-Dichloroaniline (30 g, 185 mmoles) was added in one portion as a solid. The suspension was re-cooled to −2 to 0° C. and sodium nitrite (14.4 g, 209 mmoles) dissolved in water (30 ml) was added dropwise to the acidic mixture through an addition funnel over a period of 1 hour at −2 to 0° C. The resulting mixture was stirred for 1 hour at −2 to 0° C. The mixture was then transferred in a jacketed addition funnel previously cooled to −5° C., washing the flask with cold water and added dropwise over a period of 2 hours at −2 to 0° C. to a solution of L-ascorbic acid (33 g, 187 mmoles) dissolved in water (330 ml). At the end of the addition the reaction mixture was kept at −2 to 0° C. for 10 minutes and filtered. The solid was repulped in water (600 ml) at 0° C. for 30 minutes, filtered, washed with cold water and dried under vacuum at 20–25° C. for 16 hours with 45.6 g of lactone intermediate being obtained as a yellow solid. The lactone product contained 20–25% molar of oxalic acid intermediate.

Thirty-one grams of crude lactone were triturated in i-PrOAc (200 ml) at 20–25° C. for 30 minutes, filtered and dried under vacuum at 20–25° C. for 16 hours leading to 20.2 g of a yellow crystalline solid ($^1$H-NMR spectra in DMSO-$d_6$: lactone plus 6–7% molar of oxalic acid intermediate; 45% overall yield)

$^1$H-NMR (DMSO-$d_6$) δ7.94 (broad s, 1H), 7.76 (d, J=8.6 Hz, 1H), 7.67 (dd, J=2.5, J=8.6 Hz, 1H), 7.41 (d, J=2.5 Hz, 1H), 7.12 (broad s, 1H), 5.67 (broad s, 1H), 4.64 (s, 1H), 4.40 (dd, J=3.7, J=6.0 Hz, 1H), 4.26 (dd, J=6.0, J=9.5 Hz, 1H), 3.96 (dd, J=3.7, J=9.5 Hz, 1H).

EXAMPLE 7

Preparation of 2,5-dichlorophenylhydrazine oxalic acid Intermediate

To a 500 ml flask under a nitrogen atmosphere, concentrated HCl (180 ml, 32%, 10.17 M, 1.83 moles) was charged and cooled down to −2 to 0° C. 2,5-Dichloroaniline (30 g, 185 mmoles) was added in one portion as a solid. The acidic suspension was re-cooled to −2 to 0° C. and sodium nitrite (15.3 g, 222 mmoles) dissolved in water (30 ml) was added dropwise to the acidic mixture through an addition funnel over a period of 1 hour at −2 to 0° C. The resulting mixture was kept with stirring for 1 hour at −2 to 0° C. Next, L-ascorbic acid (34.2 g, 194 mmoles) was added portionwise as a solid at −2 to 0° C. The reaction mixture was allowed to come to room temperature (18–20° C.). A thick orange suspension was formed. The reaction mixture was diluted with concentrated HCl (50 ml, 32%, 0.51 moles, 2.7 eq) and water (150 ml) and then filtered. The wet solid was triturated in water (650 ml) at 20–25° C. for 16 hours, filtered, washed with water and dried to constant weight to afford 34 g of crude oxalic acid derivative as a red crystalline solid.

Seventeen grams of crude product were triturated in $CH_2Cl_2$ (340 ml) at 40° C. for 1 hour and then filtered. The wet solid was dissolved at 40–45° C. in EtOH (340 ml) and activated charcoal (2 g) was added. The resulting mixture was stirred 45 minutes at 45–50° C., then filtered on a dicalite panel. The filtrate was concentrated under vacuum in a rotavapor to 50 ml and sitrred 16 hours at 0–5° C., leading to formation of a yellow suspension. The solid was filtered and dried to constant weight, with 5.85 g of oxalic acid intermediate being obtained as an off-white solid (25% overall molar yield).

EXAMPLE 8

Preparation of 2,5-dichlorophenylhydrazine hydrochloride

Concentrated HCl (120 ml, 32%, 1.2 moles) was charged to a 500 ml flask under a nitrogen atmosphere and cooled down to −2 to 0° C. 2,5-Dichloroaniline (20 g, 123 mmoles) was added in one portion as a solid. The reaction mixture was re-cooled to −2 to 0° C. and sodium nitrite (10.2 g, 0.148 moles) dissolved in water (20 ml) was added dropwise to the acidic solution through an addition funnel over a period of 1 hour at −2 to 0° C. The resulting mixture was stirred for 1 hour at −2 to 0° C. L-Ascorbic acid (22.8 g, 0.129 moles) was then added portionwise as a solid over a period of 1 hour at −2 to 0° C. The reaction was allowed to come to room temperature (18–20° C.) over a period of 10 minutes, then heated at 40° C. and stirred for 2 hours at this temperature. The resultant slurry was cooled to room temperature (18–20° C.) and water (50 ml) was added. The mixture was stirred 16 hours at 20–25° C., then filtered and the solid was washed with water to afford 110 g of wet oxalic acid intermediate.

One hundred eight grams of wet oxalic acid intermediate product were suspended in concentrated HCl (160 ml) and water (90 ml) and stirred at 90° C. for 2 hours. The orange suspension was cooled and stirred for 16 hours at 20–25° C. The solid was filtered and dried to constant weight, resulting in 22.4 g of 2,5-dichlorophenylhydrazine.HCl.xH$_2$O (x=2–3) as an orange solid (HPLC purity calculated as area percent: 98.3%; 71% overall molar yield based on a molecular weight of 260.34 for 2,5-dichlorophenylhydrazine monohydrochloride with 2.6 molecules of crystallization water).

EXAMPLE 9

Preparation of 2-chlorophenylhydrazine: oxalic acid Intermediate

To a 500 ml flask under a nitrogen atmosphere, concentrated HCl (80 ml, 32%, 0.81 moles) was charged and cooled to −2 to 0° C. 2-Chloroaniline (16 ml, 19.4 g, 0.15 moles) was added dropwise at −2 to 0° C. Sodium nitrite (12.4 g, 0.18 moles) dissolved in water (25 ml) was added dropwise to the acidic mixture through an addition funnel over a period of 30 minutes at −2 to 0° C. The resulting mixture was stirred for 1 hour at −2 to 0° C. L-Ascorbic acid (26.6 g, 0.15 moles) dissolved in water (130 ml) was added through an addition funnel over a period of 1 hour at −2 to 0° C. The reaction was allowed to come to room temperature (18–20° C.) over a period of 30 minutes, then heated to 40° C. and stirred for 3 hours at that temperature, cooled and stirred overnight at 18–20° C. The resultant orange slurry was filtered; the solid was washed with water, then repulped three times in hot methylene chloride (450 ml) and finally in water (115 ml) at 30° C. The product was dried to constant weight to afford 20.4 g of 2-chlorophenylhydrazido oxalic acid as a yellow solid (HPLC purity calculated as area percent:>99%).

$^1$H-NMR (DMSO-d$_6$) δ10.77. (br. s, 1H, OH), 7.69 (dd, J=7.8, 1.22 Hz, 1H), 7.18 (ddd, J=1.2, 7.5, 8.1 Hz, 1H), 6.78 (m, 2H).

EXAMPLE 10

2-Chlorophenylhydrazine hydrochloride

Concentrated HCl (100 ml, 32%, 1.0 mole) was charged to a 500 ml flask under a nitrogen atmosphere and cooled down to −2 to 0° C. 2-Chloroaniline (16 ml, 19.4 g, 0.15 moles) was added and the reaction mixture was re-cooled to −2 to 0° C. Sodium nitrite (12.6 g, 0.18 moles) dissolved in water (30 ml) was added dropwise to the acidic mixture through an addition funnel over a period of 40 minutes at −2 to 0° C. The resulting mixture (yellow suspension) was stirred for 1 hour at −2 to 0° C. L-Ascorbic acid (27 g, 0.15 moles) was then added in portions as a solid over a period of 45 minutes at −2 to 0° C. The reaction was allowed to come to room temperature (18–20° C.), then heated to 40° C. and stirred for 3 hours at this temperature. The resultant slurry was cooled to room temperature (18–20° C.) and water (100 ml) was added. The mixture was stirred for 16 hours at 20–25° C., cooled and stirred at 0–2° C. for 1 hour, then filtered and the solid was washed with water to afford 94.5 g of wet 2-chlorophenylhydrazido oxalic acid.

Ninety-four and one-half grams of wet product were suspended in concentrated HCl (120 ml) and water (30 ml) and stirred for 6 hours at 70° C. The reaction mixture (red suspension) was cooled and stirred for 16 hours at 20–25° C. The solid was filtered, washed with isopropyl alcohol and dried to constant weight, leading to 28.4 g of crude 2-chlorophenylhydrazine as a red-brownish solid.

The crude product was repulped first in water at 18–20° C. (6 vol), then in hot methylene chloride (12 vol), leading to 8.2 g of dry product. A second crop (9.5 g) was recovered from the aqueous mother liquors and combined with the first crop in methylene chloride (4 vol). After filtration and drying to constant weight, 17.4 g of 2-chlorophenylhydrazine hydrochloride hydrate were obtained as a red solid (HPLC purity calculated as area percent: 94.5%).

EXAMPLE 11

Preparation of 2-bromophenylhydrazine: oxalic acid Intermediate

To a 250 ml flask under a nitrogen atmosphere, concentrated HCl (50 ml, 32%, 0.51 moles) was charged and cooled down to −2 to 0° C. 2-Bromoaniline (10 g, 0.058 moles) was added in one portion as a solid. The acidic suspension was re-cooled to −2 to 0° C. and sodium nitrite (4.8 g, 0.070 moles) dissolved in water (10 ml) was added dropwise to the acidic mixture through an addition funnel over a period of 40 minutes at −2 to 0° C. The resulting mixture (yellow suspension) was stirred for 1 hour at −2 to 0° C. L-Ascorbic acid (10.3 g, 0.058 moles) was then added in portions as a solid at −2 to 0° C. over a period of 45 minutes. The reaction mixture (orange suspension) was allowed to come to room temperature (18–20° C.), then heated to 40° C. and stirred for 3 hours at this temperature. A red suspension was formed. The reaction mixture was cooled and stirred for 2 hours at 0–5° C. The slurry was filtered, washed with water and dried to constant weight to afford 14.3 g of crude 2-bromophenylhydrazido oxalic acid as an orange crystalline solid.

Fourteen grams of crude product were triturated first in hot methylene chloride (200 ml), then in water (140 ml) at 40° C. and finally dried to constant weight: 10.6 g of 2-bromophenylhydrazido oxalic acid were obtained as a pale brownish solid (HPLC purity calculated as area percent:>99%).

$^1$H-NMR (DMSO-d$_6$) δ10.78. (br. s, OH), 7.44 (d, 2H, NH+ArH), 7.20 (ddd, J=1.2, 7.5, 8.1 Hz, 1H), 6.70 (m, 2H, ArH).

EXAMPLE 12

2-Bromophenylhydrazine hydrochloride

Concentrated HCl (50 ml, 32%, 0.5 mole) was charged to a 250 ml flask under a nitrogen atmosphere and cooled down to −2 to 0° C. 2-Bromoaniline (10 g, 0.058 moles) was added and the reaction mixture was re-cooled to −2 to 0° C. Sodium nitrite (4.8 g, 0.070 moles) dissolved in water (10 ml) was added dropwise to the acidic mixture through an addition funnel over a period of 35 minutes at −2 to 0° C. The resulting mixture (yellow suspension) was stirred for 1 hour at −2 to 0° C. L-Ascorbic acid (10.3 g, 0.058 moles) was then added portionwise as a solid over a period of 25 minutes at −2 to 0° C. The reaction was allowed to come to room temperature (18–20° C.), then heated to 40° C. and stirred for 3 hours at this temperature. The resulting slurry (red suspension) was cooled to room temperature (18–20° C.) and water (30 ml) was added. The mixture was stirred for 16 hours at 20–25° C., cooled and stirred at 0–2° C. for 1 hour, then filtered and the solid was washed with water to afford 40 g of wet 2-bromophenylhydrazido oxalic acid.

Forty grams of wet product were suspended in concentrated HCl (60 ml) and water (15 ml) and stirred at 80° C. for 2 hours. The reaction mixture (orange suspension) was cooled and stirred for 1.5 hours at 15° C. The solid was filtered, washed with isopropyl alcohol and dried to constant weight, leading to 11.5 g of crude 2-bromophenylhydrazine as an orange solid. Eleven grams of the crude product were repulped first in water at 18–20° C. (10 vol), then in hot methylene chloride (13.5 vol), affording 2.5 g of dry product. A second crop was recovered from the aqueous mother liquors and combined with the first crop in methylene chloride (2 vol). After filtration and drying to constant weight, 7.0 g of 2-bromophenylhydrazine hydrochloride hydrate were obtained as a yellow solid (HPLC purity calculated as area percent: 96.3%).

EXAMPLE 13

Preparation of 5-cyclopropyl-1-quinolin-5-yl-1H-pyrazole-4-carboxylic acid

A 200 liter glass-lined reactor under nitrogen was charged with ethyl acetate (51 liters), methyl-3-cyclopropyl-3-oxopropanoate (4.90 kg) and N,N-dimethylformamide dimethylacetal (4.31 kg). The reactor was heated to about 75° C. for four hours at which time thin-layer chromatography analysis (ethyl acetate/hexanes, 1/1) of the reaction solution indicated that conversion to α-[(dimethylamino)methylene]-β-oxo-cyclopropanepropanoic acid, (αZ)-methyl ester was complete.

The reactor was cooled to about 20° C. and the vessel was charged with 5-hydrazinoquinoline dihydrochloride (10.0 kg). Triethylamine (15.0 liters) was added to the reactor over about a one hour period to control the heat of neutralization. The reactor was then heated to about 75° C. under nitrogen and maintained at that temperature for four hours. An HPLC assay of the reaction solution indicated that the formation of 5-cyclopropyl-1-quinolin-5-yl-1H-pyrazole-4-carboxylic acid methyl ester was complete. The reactor was then cooled to about 20° C. and ethyl acetate (17 liters) was added along with activated carbon (500 g) and filter aid (1.64 kg). A solution consisting of 66 liters of water and citric acid (20.7 kg) was also added. The resulting suspension was agitated for 1 hour and then filtered. The filter was rinsed with 15 liters of ethyl acetate.

The filtrate formed two liquid layers upon standing. The lower, dark red aqueous layer was decanted and discarded. The upper, red organic layer was transferred to a 200 liter glass-lined reactor configured for vacuum distillation. The red organic layer was distilled-down to a volume of 25 liters under reduced pressure. Propan-2-ol (31 liters) was added to the distillation pot and the volume was distilled-down to 31 liters under reduced pressure. A second propan-2-ol (31 liters) charge was made to the distillation pot and the volume was again reduced by vacuum distillation to 34 liters.

The distillation apparatus was cooled to about 20° C. and reconfigured for reflux. Aqueous NaOH (50% solution, 6.90 kg) was added to the reconfigured apparatus containing the 5-cyclopropyl-1-quinolin-5-yl-1H-pyrazole-4-carboxylic acid methyl ester/isopropanol solution. The reactor was then heated to about 75° C. under nitrogen and maintained at that temperature for four hours. An HPLC assay of the reaction solution indicated that the conversion to 5-cyclopropyl-1-quinolin-5-yl-1H-pyrazole-4-carboxylic acid was complete. The reactor was then cooled to about 20° C. and the pH of the contents was adjusted to about 4 using concentrated hydrochloric acid (about 37%). A brown suspension of solids formed as the pH was adjusted.

The solids were isolated by filtration, rinsed with $H_2O$ and dried under vacuum at about 45° C.

Yield was 6.10 kg of 5-cyclopropyl-1-quinolin-5-yl-1H-pyrazole-4-carboxylic acid, as a brown solid.

Molar Yield: 63.4% (over 3 steps based on methyl-3-cyclopropyl-3-oxopropanoate; 50.8% (based on 5-hydrazinoquinoline dihydrochloride input).

EXAMPLE 14

Purification of 5-cyclopropyl-1-quinolin-5-yl-1H-pyrazole-4-carboxylic acid

A glass-lined 100 liter reactor was charged with 56 liters of $H_2O$ and 5-cyclopropyl-1-quinolin-5-yl-1H-pyrazole-4-carboxylic acid (5.60 kg). The pH of the resulting slurry was adjusted to about 12 using 50% aqueous sodium hydroxide. A hazy, red solution formed as the pH was adjusted. Filter aid (500 g) was added to the reactor and the suspension was stirred for more than an hour at about 20° C. Reactor contents were then filtered and the filter was rinsed with about 15 liters of $H_2O$.

The filtrate was transferred to a 100 liter glass-lined reactor and the solutions pH was adjusted to about 4 using hydrochloric acid (about 37%). 5-Cyclopropyl-1-quinolin-5-yl-1H-pyrazole-4-carboxylic acid crystallized as a white solid during pH adjustment. The solids were isolated by filtration, rinsed with $H_2O$ and vacuum dried to give 5.30 kg of white 5-cyclopropyl-1-quinolin-5-yl-1H-pyrazole-4-carboxylic acid.

Molar Yield: 94.6%.

1H NMR (DMSO-d6) d 8.94 (dd, J=1.6, 4.0, 1H), 8.15 (dd, J=0.8, 8.4, 1H), 7.87 (s, 1H), 7.85–7.83 (m, 1H), 7.71 (dd, J=1.2, 7.2, 1H), 7.59–7.51 (m, 2H), 1.79 (m, 1H), 0.69 (m, 2H), 0.51–0.47 (m, 2H).

EXAMPLE 15

Preparation of N-(5-cyclopropyl-1-quinolin-5-yl-1H-pyrazole-4-carbonyl)-quanidine.mesylate To a glass-lined 100 liter reactor, under nitrogen were charged 63 liters of toluene and 5.2 kg of 5-cyclopropyl-1-quinolin-5-yl-1H-pyrazole-4-carboxylic acid. The reactor was heated to boiling and 11 liters of distillate were collected to azeotropically dry the system. The vessel was cooled to about 40° C. and 2.4 kg of thionyl chloride were added. The reactor was heated to about 75° C. and this temperature was maintained for about 13 hours. An HPLC analysis of a sample from the vessel indicated that the formation of 5-cyclopropyl-1-quinolin-5-yl-1H-pyrazole-4-carbonyl chloride was complete. The reactor was cooled to about 20° C. and the solids present were isolated by filtration. The solids were rinsed with toluene affording a "wet cake".

The 5-cyclopropyl-1-quinolin-5-yl-1H-pyrazole-4-carbonyl chloride wet cake was charged, under nitrogen, to a 100 liter glass-lined vessel containing 64 liters of tetrahydrofuran (THF). Agitation was used to suspend the solids in the vessel.

A 200 liter glass-lined reactor under nitrogen atmosphere was charged with 31 liters of water, 5.1 kg if potassium hydroxide pellets and 3.60 kg of guanidine hydrochloride. The resulting solution was then cooled to 0–5° C. The 5-cyclopropyl-1-quinolin-5-yl-1H-pyrazole-4-carbonyl chloride/THF suspension was added to the 200 liter reactor over about 30 minutes while maintaining reactor temperature at 0–5° C. The vessel was warmed to about 20° C. and stirred for 90 minutes. HPLC analysis of a sample from the reactor indicated that the formation of N-(5-cyclopropyl-1-quinolin-5-yl-1H-pyrazole-4-carbonyl)-guanidine was complete. The agitation of the reactor was stopped and two liquid layers formed on standing. The lower aqueous layer was removed and extracted two additional times with 19 liters of THF (38 liters total). The three THF fractions were combined and stirred with activated carbon and filter aid for 1 hour at about 50° C. The suspension was filtered hot and rinsed with THF.

The filtrate was transferred to a 200 liter vessel, configured for atmospheric distillation under nitrogen. The vessel was heated to boiling and about 100 liters of distillate were collected. Ethanol (94 liters) was charged to the distillation vessel and the distillation was resumed, collecting another 94 liters of distillate. A second charge of ethanol (94 liters) was made to the distillation vessel and the distillation was resumed, collecting another 94 liters of distillate. A third charge of ethanol (94 liters) was made to the distillation vessel and the distillation was resumed, collecting another 82 liters of distillate. N-(5-cyclopropyl-1-quinolin-5-yl-1H-pyrazole-4-carbonyl)-guanidine crystallized near the end of the distillation. The vessel was then cooled to about 20° C. and the solids were isolated by filtration. The solids were rinsed with ethanol and vacuum dried, affording 5.10 kg of N-(5-cyclopropyl-1-quinolin-5-yl-1H-pyrazole-4-carbonyl)-guanidine hemi-ethanolate.

A 50 liter glass-lined reactor was charged with 44 liters of THF, 4.4 liters of dimethylsulfoxide and 4.81 kg of N-(5-cyclopropyl-1-quinolin-5-yl-1H-pyrazole-4-carbonyl)-guanidine hemiethanolate. The reactor was warmed to about 35° C. under nitrogen, forming a solution. The solution was filtered into a second vessel to remove trace insoluble material. A solution of 1246 g of methanesulfonic acid in THF (about 8 liters) was prepared in an addition flask over the vessel containing the filtrate. The vessel containing the filtrate was warmed to about 53° C. and the acid solution was added slowly over a 1 hour period. N-(5-Cyclopropyl-1-quinolin-5-yl-1H-pyrazole-4-carbonyl)-guanidine mesylate crystallized near the end of the acid addition. The solids were isolated by filtration, rinsed with THF and vacuum dried, affording 5.13 kg of N-(5-cyclopropyl-1-quinolin-5-yl-1H-pyrazole-4-carbonyl)-guanidine mesylate.

EXAMPLE 16

Illustration of Yield Improvement in 5-cyclopropyl-1-quinolin-5-yl-1H-pyrazole-4-carboxylic acid Formation Using Pure 5-hydrazinoquinoline dihydrochloride Produced by the L-ascorbic acid Reduction Methodology Methyl-3-cyclopropyl-3-oxopropanoate (24.5 g, 0.1723 mole), N,N-dimethylformamide dimethyl acetal (21.56 g, 0.181 mole) and ethyl acetate (255 ml) were mixed together in a reaction flask under nitrogen and the resultant yellow solution held at 64–66° C. for 3 h 20 min to form α-[(dimethylamino)methylene]-β-oxo-cyclopropanepropanoic acid, (αZ)-methyl ester. The reaction solution was then cooled to room temperature. 5-Hydrazinoquinoline dihydrochloride (40.0 g, 0.1723 mole) was added to the yellow reaction solution containing α-[(dimethylamino)methylene]-β-oxo-cyclopropanepropanoic acid, (αZ)-methyl ester to form a yellow slurry. Triethylamine, TEA (60 ml, 0.431 mole, 2.5 equivalent) was added dropwise to the yellow slurry over 10 minutes. The reaction mixture self heated to about 35° C. After the addition was complete the resultant reaction mixture was heated to the temperature range 64–66° C. The slurry turned red upon heating. After 3 hours and 45 minutes, the reaction was essentially completed as measured by HPLC. The reaction mixture was cooled to room temperature and the following was added to the reaction mixture: ethyl acetate (170 ml), water (306 ml), citric acid (78.2 g, 0.407 mole) and Celite® filter aid (15 g). The quenched reaction liquors were stirred for 40 min. at 22–24° C., and then filtered to remove insoluble red material and filter aid. The filter cake was washed with a further 75 ml of ethyl acetate and the filtrate and wash were combined. The filter cake was discarded. The liquids were allowed to separate into two layers, a red organic layer (about 450 ml) and a dark red aqueous layer (about 550 ml). The red organic layer was concentrated under vacuum to a volume of about 150 ml. Propan-2-ol (150 ml) was added to the ethyl acetate concentrate and again concentrated to 150 ml under vacuum. A further quantity of propan-2-ol (150 ml) was added to the concentrate and this was finally concentrated to about 175 ml. The concentrate obtained contained the pyrazole ester, 5-cyclopropyl-1-quinolin-5-yl-1H-pyrazole-4-carboxylic acid methyl ester. Under a nitrogen atmosphere, water (50 ml) and 50% sodium hydroxide solution (22.5 ml, 0.431 mole) was added to the concentrate containing 5-cyclopropyl-1-quinolin-5-yl-1H-pyrazole-4-carboxylic acid methyl ester. A blue solution was formed and self-heating to about 31° C. was observed. The blue reaction mixture was heated to 64–66° C. and held under a nitrogen atmosphere for 4 h at this temperature. The reaction was found to be complete by HPLC testing and was cooled to room temperature. Concentrated hydrochloric acid 32% (about 33 ml) was added to the reaction mixture to adjust the pH to 4. Cooling was applied during the pH adjustment and the resultant yellow crystal slurry obtained was stirred at 15–20° C. for 1 h before isolation by filtration. The filter cake product was washed with water (80 ml) and dried under vacuum at 45° C. until all water was removed to afford 36.86 g 5-cyclopropyl-1-quinolin-5-yl-1H-pyrazole-4-carboxylic acid as pale pink crystals. Molar yield 76.6% based on input of 5-hydrazinoquinoline dihydrochloride.

Although certain presently preferred embodiments of the invention have been described herein, it will be apparent to those skilled in the art that variations and modifications of the described embodiments may be made without departing from the spirit and scope of the invention.

What is claimed is:

1. N-(5-Cyclopropyl-1-quinolin-5-yl-1H-pyrazole-4-carbonyl)-quanidine or a pharmaceutically acceptable salt thereof having a light absorption at 450 nanometers of less than about 0.020 in a 1% water solution at 25° C.

2. N-(5-Cyclopropyl-1-quinolin-5-yl-1H-pyrazole-4-carbonyl)-quanidine monomesylate having a light absorption at 450 nanometers of less than about 0.02 in a 1% water solution at 25° C.

3. The compound of claim 1 wherein the light absorption is less than about 0.01.

4. The compound of claim 2 wherein the light absorption is less than about 0.01.

5. A pharmaceutical composition comprising a compound of claim 1 and a pharmaceutically acceptable vehicle, diluent or carrier.

6. A pharmaceutical composition comprising a compound of claim 2 and a pharmaceutically acceptable vehicle, diluent or carrier.

7. A pharmaceutical composition comprising a compound of claim 3 and a pharmaceutically acceptable vehicle, diluent or carrier.

8. A pharmaceutical composition comprising a compound of claim 4 and a pharmaceutically acceptable vehicle, diluent or carrier.

9. A method of reducing tissue damage resulting from ischemia or hypoxia comprising administering to a mammal in need of such treatment a therapeutically effective amount of the compound of claim 1 or a pharmaceutically acceptable composition comprising said compound.

10. A method of reducing tissue damage resulting from ischemia or hypoxia comprising administering to a mammal in need of such treatment a therapeutically effective amount of a compound of claim 2 or a pharmaceutically acceptable composition comprising said compound.

11. A method of reducing tissue damage resulting from ischemia or hypoxia comprising administering to a mammal in need of such treatment a therapeutically effective amount of a compound of claim 3 or a pharmaceutically acceptable composition comprising said compound.

12. A method of reducing tissue damage resulting from ischemia or hypoxia comprising administering to a mammal in need of such treatment a therapeutically effective amount of a compound of claim 4 or a pharmaceutically acceptable composition comprising said compound.

* * * * *